United States Patent [19]

Kimura et al.

[11] 4,057,684

[45] Nov. 8, 1977

[54] ALKYL AMINO-GLUCOPYRANOSIDE DERIVATIVE AND PROCESS FOR PRODUCING THE SAME

[75] Inventors: Goro Kimura, Kamakura; Junzo Sekine, Tokyo, both of Japan

[73] Assignee: Tokyo Tanabe Company, Limited, Japan

[21] Appl. No.: 588,893

[22] Filed: June 20, 1975

[30] Foreign Application Priority Data

July 5, 1975 Japan .................................. 50-76975

[51] Int. Cl.$^2$ ...................... A61K 31/70; C07H 15/04
[52] U.S. Cl. ........................................ 536/4; 424/180; 536/18; 536/53
[58] Field of Search ...................... 260/211 R, 210 R; 536/4, 18, 53

[56] References Cited

U.S. PATENT DOCUMENTS

| 2,235,783 | 3/1941 | White | 260/210 R |
|---|---|---|---|
| 2,355,245 | 8/1944 | Schreiber et al. | 260/210 R |
| 3,073,788 | 1/1963 | Hostettler et al. | 260/210 R |
| 3,577,406 | 5/1971 | Hessler | 260/211 R |
| 3,767,640 | 10/1973 | Suami et al. | 260/211 R |

Primary Examiner—Johnnie R. Brown
Attorney, Agent, or Firm—McGlew and Tuttle

[57] ABSTRACT

Certain alkyl amino-glucopyranoside are disclosed, including alkyl N-carbamyl-N'-(2-chloroethyl)-N'-nitroso-6-amino-6-deoxy-D-glucopyranoside, alkyl N-carbamyl-N'-(2-chloroethyl)-N'-nitroso-2-amino-2-deoxy-D-glucopyranoside, and alkyl di-N,N'-[N-(2-chloroethyl)-N-nitroso-carbamyl]-2,6-di-amino-2,6-dideoxy-D-glucopyranoside. The alkyl amino-glucopryanoside exhibits marked antitumor activity while not having diabetogenic activity and bone marrow toxicity. The alkyl amino-glucopryanoside is further water soluble and free from antibacterial activity.

11 Claims, No Drawings

ALKYL AMINO-GLUCOPYRANOSIDE DERIVATIVE AND PROCESS FOR PRODUCING THE SAME

The present invention relates to novel compounds possessing a potent anticancer activity. More particularly, the invention relates to alkyl amino-glucopyranoside represented by the following formula:

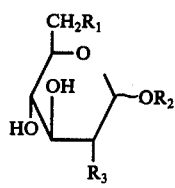

wherein $R_2$ is an alkyl group having 1–4 carbon(s); and each of $R_1$ and $R_3$ is an N-carbamyl-N'-(2-chlorethyl)-N'-nitroso-amino group (i.e.,—NHCON(NO)—CH$_2$CH$_2$Cl) or hydroxyl group, except however when both of $R_1$ and $R_3$ are hydroxyl groups. The invention also relates to a process for producing the same.

It has hitherto been well known that N-carbamyl-N'-methyl-N'-nitroso-2-amino-2-deoxy-D-glucopyranose, so-called streptozotocin, exhibits an antitumor activity, and it has recently been reported that 2-[3-(2-chloroethyl)-3-nitrosoureido]-2-deoxy-D-glucopyranose, which is a water-soluble derivative of said streptozotocin, exhibits an improved antitumor activity, while having low bone marrow toxicity (T. Anderson et al.: Proc. Am. Assoc. Cancer Res., 15, 65th Meet. 60(1974)). However, this nitrosoureido compound suffered, like streptozotocin, from the defect that it was diabetogenic in test animals. In contrast, the tetraacetate of said nitrosoureido compound, that is, 3-(tetraacetyl glucopyranos-2-yl)-1-(2-chloroethyl)-1-nitrosourea (hereinafter abbreviated to GCNU) has further been reported to exhibit 137% increase in life span of the test animals, without causing leukopenia, with a single i.p. administration at a dose of 15 mg/kg in leukemia L-1210 implanted mice, while it has nondiabetogenic activity and reduced bone marrow toxicity (P.S. Schein et al.: Cancer Research., 33, 2005(1973)). However, GCNU suffers from a large defect in that it is water-insoluble.

The amino-glucopyranoside [I] of the present invention, which is rather structurally dissimilar to streptozotocin, is water-soluble and has marked antitumor activity, while being free from diabetogenic and antibacterial activities. The alkyl amino-glucopyranoside [I] has further reduced bone marrow toxicity.

The amino-glucopyranoside [I] of the invention includes the following three groups of compounds:

Alkyl N-carbamyl-N'-(2-chloroethyl)-N'-nitroso-6-amino-6-deoxy-D-glucopyranoside . . . [I-1]

Alkyl N-carbamyl-N'-(2-chloroethyl)-N'-nitroso-2-amino-2-deoxy-D-glucopyranoside . . . [I-2]

Alkyl di-N,N'-[N-(2-chloroethyl)-N-nitroso-carbamyl]-2,6-di-amino-2,6-di-deoxy-D-glucopyranoside . . . [I-3]

The glucopyranoside [I] of the invention may be produced, as shown in the undermentioned reaction formula, produced by subjecting the compound having the formula [II] or its acid addition salt to condensation-reaction with 2-chlorethyl isocyanate, [IV], to obtain the compound of the formula [III], followed by nitrosation of said compound [III]:

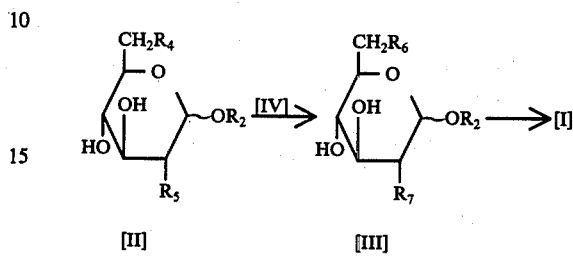

wherein $R_2$, $R_1$, and $R_3$ are the same groups as previously defined, respectively; each of $R_4$ and $R_5$ is an hydroxyl or an amino group, except, however, when both $R_4$ and $R_5$ are hydroxyl groups; and each of $R_6$ and $R_7$ is an N-carbamyl-N'-(2-chloroethyl)-amino group or an hydroxyl group, except, however, when both $R_6$ and $R_7$ are hydroxyl groups; on the other hand, [IV] shows 2-chloroethyl isocyanate (i.e., ClCH$_2$CH$_2$NCO).

By way of explanation more particularly, in order to produce the compound [I-1] according to the invention, the compound of the formula [II] wherein $R_4$ is an amino group and $R_5$ is an hydroxyl group, (that is, alkyl 6-amino-6-deoxy-D-glucopyranoside, [II-1]), is employed as starting material, and thereby the compound of the formula [III] wherein $R_6$ is an N-carbamyl-N'-(2-chloroethyl)-amino group and $R_7$ is an hydroxyl group, (that is, alkyl N-carbamyl-N'-(2-chloroethyl)-6-amino-6-deoxy-D-glucopyranoside, [III-1]), is obtained, and this compound [III-1] is then nitrosated.

Likewise, for the production of the compound [I-2] of the invention, the compound of the formula [II] wherein $R_4$ is an hydroxyl group and $R_5$ is an amino group, (that is, alkyl 2-amino-2-deoxy-D-glucopyranoside, [II-2]), is employed to afford the compound of the formula [III] wherein $R_6$ is an hydroxyl group and $R_7$ is an N-carbamyl-N'-(2-chloroethyl)-amino group, (that is, alkyl N-carbamyl-N'-(2-chloroethyl)-2-amino-2-deoxy-D-glucopyranoside, [III-2]; and this compound [III-2] is then nitrosated.

Furthermore, to produce the compound [I-3], the compound of the formula [II] wherein both $R_4$ and $R_5$ are amino groups, (that is, alkyl 2,6-di-amino-2,6-dideoxy-D-glucopyranoside, [II-3]), is employed to obtain the compound of the formula [III] wherein both $R_6$ and $R_7$ are N-carbamyl-N'-(2-chloroethyl)-amino groups, (that is, alkyl di-N,N'-[N-(2-chloroethyl)-carbamyl]-2,6-di-amino-2,6-di-deoxy-D-glucopyranoside, [III-3]; this is followed by nitrosation of said compound [III-3]).

The amino-glucopyranoside [I] of the present invention is, as seen from the above-mentioned, produced through the following three reaction routes:

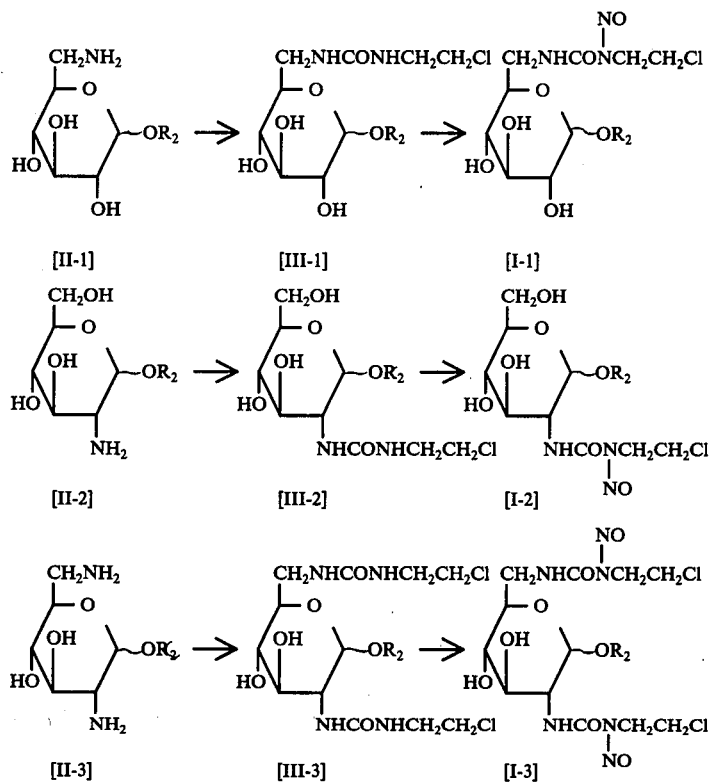

Furthermore, the glucopyranoside [I] of the present invention has two anomers substantially, that is, α-anomer and β-anomer, however the compound of either anomer, and further the mixture of the compounds of these two anomers all possess marked antitumor activity. Such compound [I] of α-anomer or β-anomer may be produced by using the corresponding compound [II] of α-anomer or β-anomer, respectively. The same may be said of the mixture of the compounds [I] of α-anomer and β-anomer.

In the process for producing the amino-glucopyranoside [I] of the invention, the condensing reaction of the first step proceeds favourably in a suitable solvent, at a temperature ranging from −15° C to reflux temperature of the solvent used. The compound of formula [II] may be used in the form either of free base or of addition salt or inorganic or organic acid such as hydrochloric acid, sulfric acid, phosphoric acid, glacial acetic acid, oxalic acid or succinic acid. When using the above-mentioned acid addition salt, it is desirable to add a deacidifying agent in the reaction system. As the deacidifying agent, metallic carbonate such as silver carbonate may be employed, alkali earth metal carbonate or heavy metal carbonate; tertiary amines such as trimethylamine, triethylamine, tripropylamines, tributylamines, triamylamines, pyridine or quinoline may also be used; or an anion-exchange resin such as an amino-type may be used.

Some useful solvents in the above condensing reaction are the following: aliphatic, alicyclic or aromatic, mono- or poly-hydric alcohols having 1–12 carbon(s); sulfur-containing compounds such as dimethylsulfoxide or tetramethylenesulfone; and phosphorous-containing compound such as hexamethyl-phosphoramide. Mixtures of solvents are also useful water may also be suitably used, as well as aqueous solvents and solvents such as nitriles, hydrocarbons, hydrocarbon halides, ketones, esters, ethers, alcohols, sulfur-containing compounds or phosphorous-containing compound; said alcohols and the latter two groups of the compounds having the same meanings as previously defined, respectively.

The nitrosating reaction of the compound [III] in second step of the present process may be accomplished in a known manner. For example, this reaction proceeds suitably by either causing one member selected from nitrous acid, nitrite and nitrous alkyl to react with the compound [III] in the presence of organic or inorganic acid such as hydrochloric acid, sulfuric acid, phosphoric acid, acetic acid, formic acid or the like, or causing nitrosylchloride to react with the compound [III] in a mixture of acetic acid with sodium acetate. This reaction may be carried out favorably at a temperature of −15° C ∼50° C. The desired compound [I] which is thus formed may be readily separated from the reaction solution and purified through known purification procedures, such as ion-exchange resin treatment, column chromatography and recrystallization from organic solvent.

Results of pharmacological studies for amino-glucopyranoside [I] according to the invention are described below. The test compounds which were used included methyl N-carbamyl-N'-(2-chloroethyl)-N'-nitroso-2-amino-2-deoxy-α-D-glucopyranoside and methyl N-carbamyl-N'-(2-chloroethyl)-N'-nitroso-6-amino-6-deoxy-α-D-glucopyranoside (hereinafter abbreviated to 2MCαG and 6MCαG, respectively). The control compounds which were employed were 1-(2-chloroethyl)-3-cyclohexyl-1-nitrosoourea (hereinafter abbreviated to CCNU), which had been widely applied as a control compound in such a pharmacological test of the streptozotocin derivatives, and GCNU referred to previously. The tumor systems which were used were leukemia L-1210, Nakahara-Fukuoka sarcoma, adenocarcinoma-755, ascites sarcoma 180 and Ehrlich ascites carcinoma (hereinafter abbreviated to L-1210, NFS, Ca-755, S-180A and EAC, respectively), and the antitumor activities were determined by a procedure of the National Cancer Center, Tokyo (A. Hoshi et al.: Farumashia 9, 464(1973)). The test animals which were used were ICR and BDF$_1$ mice.

Table I presents the antitumor effects of 2MCαG against various tumor systems. As could be observed, 2MCαG, at a dosage of 12.5 mg/kg/day administered to mice intraperitoneally for 5 successive days exhibited activities of ++ and +++ against NFS, Ca-755, S-180A and EAC; in particular, it was more effective than CCNU against NFS and Ca-755; while with the same schedule but at dosage of 3.2 mg/kg/day, no accumulation of ascites tumor cells was observable in S-180A and EAC implanted mice. Against L-1210, at a dose of 3.2 mg/kg/day administered intraperitoneally for 5 successive days, 3 out of 6 mice survived and an increase in life span (abbreviated to ILS) of 394% was observed; and with the same schedule but at 6.3 mg/kg/day administered orally 2 out of 6 mice survived and an ILS of 343% was shown; while a single 10–20 mg/kg intraperitoneal administration resulted in an ILS of 717% and all 6 animals survived. These results revealed that against L-1210, a single dose of 2MCαG might be more effective than a five dose schedule thereof.

On the other hand, the LD$_{50}$ of 2MCαG with ICR mice was found to be 48 mg/kg for single dose and 16 mg/kg for 5 doses, qd. Further, an one-month administration schedule, qd, day 1–30, using male Wister rat, the blood sugar level, determination of which followed the glucose oxidase method (L. L. Saloman et al.: Anal. Chem., 31, 453(1959)), exhibited neither elevation nor depression tendencies. Using the broth dilution method, 2MCαG was also found to be without any antibacterial activities.

Table II presents the antitumor effects of 6MCαG against various tumor systems. As can be observed from the Table, 6MCαG was more active than CCNU against either NFS or Ca-755 when administered for 5 successive days intraperitoneally. The LD$_{50}$ of 6MCαG with a single administration was found to be 91 mg/kg., which value showed that 6MCαF was less toxic than 2MCαG.

Against L-1210, at a dose of 6–25 mg/kg/day for 5 successive administrations of 6MCαG either intraperitoneally or orally, 4–5 out of 6 animals survived and observed an ILS of 520–645% was observed; while in single intraperitoneal administration, a dose of 35–45 mg/kg results in an ILS of 717% and all six animals survived. Furthermore, 6MCαG was, like 2MCαG, free from diabetogenic and antibacterial activities.

Table III shows the results of test of the peripheral white blood counts (abbreviated to WBC) and survival in normal male ICR mice after treating with the test compounds.

Such peripheral white blood cell counts were performed as follows: Normal male ICR mice were used in groups of tens and the test compounds for treatment were made into their respective solutions. 2MCαG and 6MCαG were dissolved in physiological saline solutions, while CCNU and GCNU were suspended in 0.5% CMC aqueous solution and 50% PEG aqueous solution, respectively. A single administration at volume of 1 ml per 100 g body weight of animal (0.1 ml/10 g) was given intraperitoneally, and the peripheral white blood cell counts were performed 3, 8 and 15 days after administration of the test compounds.

As seen from Table III, using LD$_{10}$ doses of 2MCαG and 6MCαG, the incidence of leukopenia was comparatively mild with rapid return to pretreatment levels, which revealed that these compounds had an improved bone marrow toxicity. Compared with CCNU, 2MCαG and 6MCαG were less toxic and exhibited equivalent values as GCNU, while the acute toxicity of 6MCαG was much lower than that of either GCNU or CCNU.

The above test data reveal that the model compounds of this invention, 2MCαG and 6MCαG, are more active against L-1210, compared with CCNU and GCNU, and these model compounds have further activity against solid as well as ascites tumor systems. The compounds of this invention are water soluble and are void of diabetogenic and antibacterial activities. Moreover, they exhibit antitumor activity even when administered orally, which property has not hitherto been found in any convention compounds and which property may be regarded as characteristic of the compounds of this invention.

Table I

| Tumor system | Test mice | Test compound | Dosage mg/kg/day | Treatment[a] route | schedule | T/C[b] % | Activity[c] (died/used) | ILS[d] % | Survivors[e] |
|---|---|---|---|---|---|---|---|---|---|
| NFS | ICR | 2MCαG | 3.2 | ip | D$_{1-5}$ | 86.1 | — | | |
| | | | 6.3 | | | 55.2 | + | | |
| | | | 12.5 | | | 44.3 | ++ | | |
| | | | 15.0 | | | 29.2 | ++ | | |
| | | | 20.0 | | | — | Toxic (6/6) | | |
| | | CCNU | 20.0 | | | 48.3 | ++ | | |
| Ca-755 | BDF$_1$ | 2MCαG | 3.2 | ip | D$_{1-5}$ | 22.4 | ++ | | |
| | | | 6.3 | | | 9.6 | +++ | | |
| | | | 12.5 | | | 3.3 | +++ | | |
| | | | 15.0 | | | 0.3 | Toxic (6/6) | | |
| | | CCNU | 10.0 | | | 15.0 | +++ | | |
| S 180A | ICR | 2MCαG | 3.2 | ip | D$_{1-5}$ | 0 | +++ | | |
| | | | 12.5 | | | 0 | +++ | | |
| EAC | ICR | 2MCαG | 3.2 | ip | D$_{1-5}$ | 0 | +++ | | |
| | | | 12.5 | | | 0 | +++ | | |
| L-1210 | BDF$_1$ | 2MCaαG | 1.0 | ip | D$_{1-5}$ | | | 48 | 0/6 |
| | | | 2.0 | | | | | >249 | 1/6 |
| | | | 3.2 | | | | | >394 | 3/6 |
| | | | 4.0 | | | | | >349 | 2/6 |
| | | | 6.3 | | | | | >198 | 1/6 |
| | | | 10.0 | | | | | >190 | 1/6 |
| | | | 12.5 | | | | | >160 | 1/6 |
| | | | 20.0 | | | | | 58 | 0/6 |
| | | 2MCαG | 2.0 | po | D$_{1-5}$ | | | >143 | 1/6 |
| | | | 3.2 | | | | | >141 | 1/6 |
| | | | 6.3 | | | | | >343 | 2/6 |
| | | | 12.5 | | | | | 211 | 0/6 |

Table I-continued

| Tumor system | Test mice | Test compound | Dosage mg/kg/day | Treatment[a] route | Treatment[a] schedule | T/C[b] % | Activity[c] (died/used) | ILS[d] % | Survivors[e] |
|---|---|---|---|---|---|---|---|---|---|
| | | 2MCαG | 6.3 | ip | D₁ | | | 128 | 0/6 |
| | | | 8.0 | | | | | >432 | 3/6 |
| | | | 10.0 | | | | >717 | 6/6 | |
| | | | 20.0 | | | | | >717 | 6/6 |
| | | | 25.0 | | | | | >539 | >4/6 |

[a]Treatment was initiated 24 hr after implantation of tumor (day 1):D₁₋₅ = qd, day 1∼5; D₁ = day 1 only.
[b]T/C is expressed as the tumor weight ratio in solid tumors or total packed cellvolume ratio in ascites tumors of treated/control.
[c]% of T/C as activity is graded in the following manner: 100∼71% = −;70∼51% = +; 50∼21% = ++; 20∼0% = +++ in cases of solid tumors. 100∼66% = −;65∼41% = +; 40∼11% = ++; 10∼0% 10∼0% = +++ in cases of ascites tumors.
[d]% increase in life span (mean survival time) over controls.
[e]60 days survivors/total in treated group.

Table II

| Tumor system | Test mice | Test compound | Dosage mg/kg/day | Treatment[a] route | Treatment[a] schedule | T/C[b] % | Activity[c] (died/used) | ILS[d] % | Survivors[e] |
|---|---|---|---|---|---|---|---|---|---|
| NFS | ICR | 6MCαG | 12.5 | ip | D₁₋₅ | 77.8 | − | | |
| | | | 25.0 | | | 61.6 | + | | |
| | | | 35.0 | | | 38.8 | ++ | | |
| | | | 50.0 | | | 34.1 | Toxic (6/6) | | |
| | | CCNU | 12.0 | | | 57.5 | + | | |
| | | | 20.0 | | | 48.3 | ++ | | |
| Ca-755 | BDF₁ | 6MCαG | 6.3 | ip | D₁₋₅ | 53.4 | + | | |
| | | | 12.5 | | | 16.3 | +++ | | |
| | | | 25.0 | | | 7.6 | +++ | | |
| | | | 50.0 | | | 0 | Toxic (6/6) | | |
| | | CCNU | 10.0 | | | 15.0 | +++ | | |
| | | | 25.0 | | | 1.1 | Toxic (6/6) | | |
| L-1210 | BDF₁ | 6MCαG | 3.0 | ip | D₁₋₅ | | | >292 | 2/6 |
| | | | 6.0 | | | | | >639 | 3/6 |
| | | | 10.0 | | | | | >645 | 3/6 |
| | | | 12.5 | | | | | >520 | 4/6 |
| | | | 25.0 | | | | | >615 | 4/6 |
| | | | 40.0 | | | | | >237 | 2/6 |
| | | 6MCαG | 6.0 | po | D₁₋₅ | | | >580 | 4/6 |
| | | | 12.5 | | | | | >570 | 4/6 |
| | | | 25.0 | | | | | >620 | 4/6 |
| | | 6MCαG | 35.0 | ip | D₁ | | | >717 | 6/6 |
| | | | 45.0 | | | | | >717 | 6/6 |

[a],[b],[c],[d],[e]same as in Table I.

Table III

| Treatment | Dose (mg/kg, ip) | Average count and range of WBC/mm³ for 10 mice on Day (x 10²) 3 | 8 | 15 | Death rate (death/used) |
|---|---|---|---|---|---|
| 50% PEG | — | 98.0±8.8 | 134.9±14.6 | 110.7±9.9 | 0/10 |
| Saline | — | 125.0±9.9 | 118.8±19.4 | 133.8±15.7 | 0/10 |
| 0.5% CMC | — | 102.6±3.3 | 109.0±5.1 | 135.7±14.8 | 0/10 |
| 2MCαG | 10 | 74.0±4.6 | 105.6±4.5 | 131.8±5.4 | 0/10 |
| | 20 | 46.3±9.5 | 101.0±16.5 | 129.4±20.1 | 2/10 |
| | 40 | 30.8±2.8 | — | — | 10/10 |
| | 60 | 35.4±2.9 | — | — | 10/10 |
| | 80 | 32.0±3.8 | — | — | 10/10 |
| 6MCαG | 40 | 73.2±3.5 | 105.7±3.8 | 136.9±10.0 | 0/10 |
| | 60 | 41.1±4.1 | 73.5±5.8 | 110.4±6.3 | 0/10 |
| | 100 | 31.2±2.5 | 71.9±4.9 | 99.8±10.8 | 2/10 |
| | 150 | 28.1±3.8 | 61.0 | — | 10/10 |
| CCNU | 20 | 38.7±2.9 | 81.8±5.0 | 100.4±9.8 | 0/10 |
| | 40 | 31.5±1.7 | 59.0±6.0 | 77.9±9.0 | 1/10 |
| | 60 | 27.9±3.7 | 60.0 | 36.0 | 9/10 |
| | 80 | 20.4±2.5 | — | 10/10 | |
| GCNU | 10 | 83.1±4.5 | 140.3±15.7 | 116.0±10.0 | 0/10 |
| | 20 | 60.4±3.6 | 131.4±17.4 | 106.0±9.0 | 6/10 |
| | 40 | 33.2±3.3 | — | — | 10/10 |
| | 60 | 26.5±3.5 | — | — | 10/10 |

The following examples serve to illustrate the invention without however limiting it any way:

EXAMPLE 1

2.29 g of methyl 2-amino-2-deoxy-α-D-glucopyranoside hydrochloride are dissolved in 20 ml of water, and to this solution is added 30 ml of acetonitrile. Then while ice-cooling, 1.48 g of 2-chloroethyl isocyanate and 1.8 g of silver carbonate are added further. The resultant is heated under reflux on a water bath for 1 hr, and the reacted solution is filtered while hot, to remove the insoluble silver salt formed. The filtrate is evaporated in vacuo and the crystalline residue is recrystallized from ethanol to give 1.84 g of methyl N-carbamyl-N'-(2-chloroethyl)-2-amino-2-deoxy-α-D-glucopyranoside. Yield: 61.5%. mp 162°∼163° C. $[\alpha]_D^{25}$ +94.9° (C=0.5, H₂O). Beilstein test: positive. IR (KBr): 1620 cm⁻¹ (—CO), 1575 cm⁻¹ (—NH), 3300 cm⁻¹ (—NH, —OH). Analysis for $C_{10}H_{19}N_2O_6Cl$ (M.W. 298.72) (%) — C, 40.21; H, 6.41; N, 9.38; Cl, 11.87. Found: C, 40.16; H, 6.39; N, 9.41; Cl, 11.80.

6.10 g of methyl N-carbamyl-N'-(2-chloroethyl)-2-amino-2-deoxy-α-D-glucopyranoside having been prepared in the same manner as described in the above procedure are dissolved in 80 ml of 20% aqueous acetic acid solution. To this mixture is then added slowly 1.69 g of sodium nitrite while stirring with ice-cooling. The resulting solution is allowed to stand overnight in a refrigerator. To this solution are then added 27 ml of ion exchange resin (H+ form, the trade name "Amberlite IR-120"; hereinafter the same kind of resin is used), followed by stirring for 30 minutes. The ion exchange resin is filtered off and the filtrate is evaporated to dryness in vacuo at a temperature below 30° C. The crystalline residue thus obtained is recrystallized from ethanol to give 4.42 g of methyl N-carbamyl-N'-(2-chloroethyl)-N'-nitroso-2-amino-2-deoxy-α-D-glucopyranoside as pale yellowish needles. Yield: 66.1% mp 144°~146° C (decomp.). $[\alpha]_D^{23}$ +104° (C=0.5, H$_2$O). Beilstein test: positive. IR (KBr): 3370 cm$^{-1}$ (—OH), 1700 cm$^{-1}$ (—CO), 1530 cm$^{-1}$ (—NH), 1485 cm$^{-1}$ (—NO), 850 cm$^{-1}$ (α-anomeric C$_1$—H). Analysis for C$_{10}$H$_{18}$N$_3$O$_7$Cl (M.W. 327.72) (%) — C, 36.65; H, 5.54; N, 12.82; Cl, 10.82. Found: C, 36.69; H, 5.58; N, 12.78; Cl, 10.79.

EXAMPLE 2

2.42 g of methyl 2-amino-2-deoxy-α-D-glucopyranoside hemi-hydrosulfate are dissolved in 30 ml of water, and to this solution are added 40 ml of benzene-chlorform (1:1). Then, while ice-cooling, 1.4 g of 2-chloroethyl isocyanate and 2.5 g of barium carbonate are added further. The resultant mixture is heated under reflux on a water bath for 1 hr, and the so reacted solution is filtered, while hot, to remove the insoluble barium salt formed. The filtrate is evaporated in vacuo, and the crystalline residue is recrystallized from isopropanol to give 1.74 g of methyl N-carbamyl-N'-(2-chloroethyl)-2-amino-2-deoxy-α-D-glucopyranoside. Yield: 58.5%. mp 162°~163° C. $[\alpha]_D^{23}$ +95.5° (C=0.5, H$_2$O). Analysis for C$_{10}$H$_{19}$N$_2$O$_6$Cl (M.W. 298.72) (%) — C, 40.21; H, 6.41; N, 9.38; Cl, 11.87. Found: C, 40.29; H, 6.45; N, 9.31; Cl, 11.95.

2.98 g of methyl N-carbamyl-N'-(2-chloroethyl)-2-amino-2-deoxy-α-D-glucopyranoside having been prepared in the above-described manner are dissolved in 40 ml of 99% formic acid, to which are then added slowly 1.6 g of sodium nitrite powder, while stirring vigorously with ice-cooling. Such stirring is continued for 4 hr under the same conditions. The reacted solution is poured into 200 ml of ice-water, to which is then added, while stirring, 13 ml of such an ion exchange resin as has been defined previously, and followed by subsequent stirring for 20 minutes. The ion exchange resin is filtered off and the filtrate is evaporated in vacuo at a temperature below 30° C. The crystalline residue is recrystallized from ethanol to give 2.51 g of methyl N-carbamyl-N'-(2-chloroethyl)-N'-nitroso-2-amino-2-deoxy-α-D-glucopyranoside as pale yellowish crystals. Yield: 76.7%. mp 144°~146° C (decomp.). $[\alpha]_D^{22}$ +102° (C=0.5, H$_2$O). Analysis for C$_{10}$H$_{18}$N$_3$O$_7$Cl (M.W. 327.72) (%) — C, 36.65; H, 5.54; N, 12.82; Cl, 10.82. Found: C, 36.72; H, 5.51; N, 12.88; Cl, 10.78.

EXAMPLE 3

1.92 g of methyl 2,6-di-amino-2,6-di-deoxy-α-D-glucopyranoside are dissolved in 40 ml of 40% ethanol aqueous solution, to which 2.6 ml of 2-chloroethyl isocyanate are then added at 20° C while stirring vigorously. Such stirring is continued for 1 hr, while the completion of this reaction is checked by thin-layer chromatography (hereinafter abbreviated to "tlc") [silicagel; developing solvent: chloroform-ethanol (4:1); hereinafter such silicagel and solvent will mentioned in the relevant case only when they differ from the mentioned here.] The reaction solution is evaporated in vacuo at a temperature below 30° C, and the residue is crystallized from ethanol to yield 2.52 g of the crude crystals with mp 158°~162° C. These crude crystals are recrystallized from isopropanol to yield 2.17 g of methyl di-N, N'-[N-(2-chloroethyl)-carbamyl]-2,6-di-amino-2,6-dideoxy-α-D-glucopyranoside. Yield: 53.8%. mp 176°~178° C. $[\alpha]_D^{20}$ +69.6° (C=0.3, methanol). Rf 0.78 (tlc). Analysis for C$_{13}$H$_{24}$N$_4$O$_6$Cl$_2$ (M.W. 403.26) (%) — C, 38.72; H, 6.00; N, 13.89; Cl, 17.58. Found: C, 38.78; H, 6.02; N, 13.82; Cl, 17.52.

4.0 g of methyl di-N, N'[N-(2-chloroethyl)-carbamyl]-2,6-di-amino-2,6-di-deoxy-α-D-glucopyranoside prepared in the above-described manner are dissolved in 200 ml of water. To this 100 ml of 0.25N nitrous acid solution is then added dropwise at 0°~3° C while stirring with cooling. Said nitrous acid aqueous solution was prepared by passing dinitrogen trioxide gas into 100 ml of 0°~3° C water. Such stirring is continued for about 30 hours under the same conditions, and the reaction solution is lyophilized to yield crude crystals, which are then recrystallized from ethanol to give 3.14 g of methyl di-N. N'-]N-(2-chloroethyl)-N-nitroso-carbamyl]-2,6-di-amino-2,6-di-deoxy-α-D-glucopyranoside. Yield: 68.2%. mp 135°~137° C (decomp.). $[\alpha]_D^{25}$ +82° (C=0.3, methanol ). Analysis for C$_{13}$H$_{22}$N$_6$O$_8$Cl$_2$ (M.W. 461.26) (%) — C, 33.85; H, 4.81; N, 18.22; Cl, 15.37. Found: C, 33.91; H, 4.83; N, 18.27; Cl, 15.32.

The pharmacological properties of the above-mentioned compound, and the test procedures which parallel those of Table I~III, are as follows: When administered to test animals (BDF$_1$ mice) intraperitoneally at a dose of 8.5 mg/kg/day for 5 successive days, it was found to exhibit activities of ++ or +++ against NFS, Ca-755, S-180A and EAC. Against L-1210, at a dose of 2.2 mg/kg/day administered intraperitoneally for 5 successive days were observed three 60-days survivors out of six test animals and an ILS of 400%; at dosage of 4.5 mg/kg/day orally were observed three 60-days survivors out of six animals and an ILS of 370%; while for a single intraperitoneal administration at dosage of 7~15 mg/kg, all six animals tested survived the 60-days period and its ILS was 717%. This compound was also found to be nondiabetogenic and void of antibacterial activities. Furthermore, its toxicity towards the bone marrow was found to be less than that of CCNU and comparable to GCNU.

EXAMPLE 4

2.29 g of methyl 2-amino-2-deoxy-β-D-glucopyranoside hydrochloride are dissolved in 55 ml of water-isopropanol mixture (3:20). To this are then added 1.1 g of 2-chlorethyl isocyanate and 1.08 g of triethylamine while stirring with ice-cooling. The mixture is further stirred at room temperature for about 1 hr, while the completion of the reaction is checked by tlc. The reacted solution is evaporated in vacuo at a temperature below 30° C. The crystalline residue thus obtained is recrystallized from ethanol to give 1.62 g of methyl N-carbamyl-N'-(2-chloroethyl)-2-amino-2-deox-β-D-glucopyranoside. Yield: 54.3%, mp 168°~170° C. $[\alpha]_D^{25}$ −28.4° (C=0.5, H$_2$O). Analysis for C$_{10}$H$_{19}$N$_2$O$_6$Cl (M.W. 298.72) (%) — C, 40.21; H, 6.41; N, 9.38; Cl, 11.87. Found: C, 40.27; H, 6.48; N, 9.42; Cl, 11.83.

2.98 g of methyl N-carbamyl-N'-(2-chlorethyl)-2-amino-2-deoxy-β-D-glucopyranoside prepared in the same manner are dissolved in 100 ml of 1% sulfuric acid solution, to which are then added slowly 12 g of 5% nitrous acid solution while stirring with ice-cooling. Such stirring is continued for 1 day, while the completion of the reaction is checked by tlc. The reacted solution is evaporated in vacuo at a temperature below 30° C. The crystalline residue obtained is recrystallized from anhydrous methanol to give 1.87 g of methyl N-carbamyl-N'-(2-chloroethyl)-N'-nitroso-2-amino-2-deoxy-β-D-glucopyranoside. Yield: 57.2%. mp 152~154° C (decomp.). $[\alpha]_D^{25}$ −4° (C=0.5, H$_2$O). Analysis for C$_{10}$H$_{18}$N$_3$O$_7$Cl (M.W. 327.72) (%) — C, 36.65; H, 5.54; N, 12.82; Cl, 10.82. Found: C, 36.71; H, 5.54; N, 12.78; Cl, 10.89.

The compound obtained in the above description of this Example, when compared with its α anomer which was presented in Table I, was about 110~120% more effective as an antitumor agent. The present β anomer, at a dosage of 12.5 mg/kg/day administered intraperitoneally for 5 successive days exhibited activity of + + or + + + against NFS, Ca-755, S-180A and EAC. At a dose of 3.2 mg/kg/day administered for 5 successive days intraperitoneally, ascites cells accumulation was not detectable in both S-180A and EAC implanted animals. Against L-210, with the same dosage schedule, were observed for 60-days survivors out of six animals and an ILS of 480%; at 6.3 mg/kg/day administered for 5 days orally, were observed three 60-days survivors out of six animals and an ILS of 385%; while for a single intraperitoneal administration of 8~25 mg/kg were observed all six test animals surviving after 60-days and the ILS being 717%. This compound was not found to be either diabetogenic or exhibited any antibacterial activities. And at LD$_{10}$ dosage, the peripheral white blood cell count of the compound was 5~20% higher than that of the α-anomer at 3, 8 and 15 days respectively. From this, it was concluded that the bone marrow toxicity of the compound was 5~20% less than the same.

EXAMPLE 5

1.93 g of methyl 6-amino-6-deoxy-α-D-glucopyranoside are dissolved in 20 ml of water, and to this solution are added 50 ml of isopropanol. Thereafter, while stirring vigorously, 1.2 g of 2-chloroethyl isocyanate are added dropwise at room temperature. Such stirring is continued for about 2 hr, while the completion of the reaction is checked by tlc [solvent: chloroform-ethanol (3:1)]. The reacted solution is evaporated in vacuo at a temperature below 30° C. The crystalline residue thus obtained is recrystallized from anhydrous ethanol to give 1.71 g of methyl N-carbamyl-N'-(2-chloroethyl)-6-amino-6-deoxy-α-D-glucopyranoside as whitish crystals. Yield: 57.3%. mp 161°~162° C. $[\alpha]_D^{25}$ +76.4° (C=0.3, methanol). Analysis for C$_{10}$H$_{19}$N$_2$O$_6$Cl (M.W. 298.72) (%) — C, 40.21; H, 6.41; N, 9.38; Cl, 11.87. Found: C, 40.28; H, 6.45; N, 9.32; Cl, 11.92.

2.98 g of methyl N-carbamyl-N'-(2-chlorethyl)-6-amino-6-deoxy-α-D-glucopyranoside prepared in the same manner as described above in this Example are suspended in 80 ml of glacial acetic acid. To this suspension 0.7 g of sodium nitrite powder are added at 0°~5° C while stirring vigorously, to form a pale yellowish homogeneous solution. This solution is further stirred at the same temperature for 1 day, and the ion exchange resin is added thereto to remove the sodium ion. The ion exchange resin is filtered off and washed with glacial acetic acid, which filtrate and washings are combined and evaporated in vacuo. The residue thus obtained is recrystallized from isopropanol to yield 0.296 g off methyl N-carbamyl-N'-(2-chloroethyl)-N'-nitroso-6-amino-6-deoxy-α-D-glucopyranoside. Yield: 9.05%. mp 101°~103° C (decomp.). $[\alpha]_D^{25}$ +73.2° (C=0.3, methanol). Analysis for C$_{10}$H$_{18}$N$_3$O$_7$Cl (M.W. 327.72) (%) — C, 36.65; H, 5.54; N, 12.82; Cl, 10.82. Found: C, 36.59; H. 5.48; N, 12.91; Cl, 10.75.

EXAMPLE 6

1.93 g of methyl 2-amino-2-deoxy-α-D-glucopyranoside are dissolved in 30 ml of anhydrous ethanol, and to this solution 1.2 g of 2-chloroethyl isocyanate are added dropwise at 20° C while stirring vigorously. Such stirring is continued for about 1 hour under the same conditions, while the completion of the reaction is checked by tlc. The reaction solution is evaporated in vacuo at temperature below 30° C, and the residue is crystallized from ethanol to yield 2.42 g of crude crystals with mp 147°~151° C. Such crystals are recrystallized from isopropanol to give 1.70 g of methyl N-carbamyl-N'-(2-chloroethyl)-2-amino-2-deoxy-α-D-glucopyranoside. Yield: 57.2%. mp 162°~163° C. $[\alpha]_D^{25}$ +94.9° (C=0.5, H$_2$O). Analysis for C$_{10}$H$_{19}$N$_2$O$_6$Cl (M.W. 298.72) (%)— C, 40.21; H, 6.41; N, 9.38; Cl, 11.87. Found: C, 40.15; H, 6.49; N, 9.42; Cl, 11.85.

2.98 g of methyl N-carbamyl-N'-(2-chloroethyl)-2-amino-2-deoxy-α-D-glucopyranoside prepared in the same manner as describe above in this Example are dissolved in 50 ml of 2N sulfuric acid solution, and to this solution 4 ml of isoamyl nitrite are added dropwise at 0°~5° C while stirring vigorously. Such stirring is continued for 3 hr, while the completion of the reaction is checked by tlc. The reaction solution is evaporated in vacuo to yield crude crystals, which are then recrystallized from ethanol to give 2.75 g of methyl N-carbamyl-N'-(2-chloroethyl)-N'-nitroso-2-deoxy-α-D-glucopyranoside. Yield: 84.1%. mp 144°~146° (decomp.). $[\alpha]_D^{23}$ +104° (C=0.5, H$_2$O). Analysis for C$_{10}$H$_{18}$N$_3$O$_7$Cl (M.W. 327.72) (%) — C, 36.65; H, 5.54; N, 12.82; Cl, 10.82. Found: C, 36.68; H, 5.58; N, 12.76; Cl, 10.87.

Likewise, methyl N-carbamyl-N'-(2-chloroethyl)-2-amino-2-deoxy-α-D-glucopyranoside mentioned previously is treated in a similar manner to those described in the above example, except 20 ml of 2N hydrochloric acid and 3.5 ml of isobutyl nitrate are used instead of 50 ml of 2N sulfuric acid and 4 ml of isoamyl nitrate respectively, and thereby 2.7 g of methyl N-carbamyl-N'-(2-chloroethyl)-N'-nitroso-2-amino-2-deoxy-α-D-glucopyranoside is obtained. Yield: 82.6%. mp 144°~146° C (decomp). $[\alpha]_D^{23}$ + 104° (C = 0.5, H$_2$O). Analysis for C$_{10}$H$_{18}$N$_3$O$_7$Cl (M.W. 327.72) (%) — C, 36.65; H, 5.54; N, 12.82; Cl, 10/82. Found: C, 36.70; H, 5.51; N, 12.90; Cl, 10.78.

EXAMPLE 7

1.92 g of methyl 2,6-di-amino-2,6-di-deoxy-3-D-glucopyranoside are dissolved in 50 ml of methanol-acetone-ethyl acetate (1:1:1), and to this solution 2.5 g of 2-chloroethyl isocyanate are added dropwise at 12°~15° C, while stirring vigorously. Such stirring is continued for 2 hr, while the completion of the reaction is checked by tlc. The reaction solution is evaporated in vacuo at a temperature below 30° C, and the residue thus obtained is crystallized from ispropanol to yield 3.1 g of the crude crystals with mp 198°~202° C. The crude crystals are recrystallized from methanol to give 2.55 g of methyl di-N,N'-[N-(2-chloroethyl)-carbamyl]-

2,6-di-amino-2,6-di-deoxy-3-D-glucopyranoside. Yield: 63.3%. mp 227°∼229° C. $[\alpha]_D^{25}$−23° (C=0.1, methanol). Analysis for $C_{13}H_{24}N_4O_6Cl_2$ (M.W. 403.26) (%) — C, 38.72; H, 6.00: N, 13.89; Cl, 17.58. Found: C, 38.80; H, 5.98, N, 13.92; Cl, 17.55.

4.0 g of methyl di-N,N'-[N-(2-chloroethyl)-carbamyl]-2,6-di-amino-2,6-dideoxy-3-D-glucopyranoside prepared in the same manner as described in this Example are dissolved in 90% formic acid aqueous solution, and to this solution 2.2 g of potassium nitrite are slowly added at 0°∼4° C while stirring vigorously. Such stirring is continued for about 22 hours, while the completion of the reaction is checked by tlc [solvent: chloroform-ethanol (3:1)]. The reaction solution is allowed to stand overnight at 0° C. To the chilled solution are added 24 g of the ion exchange resin, and the mixture is stirred for 30 minutes while maintaining the mixture at 0°∼4° C. The ion exchange resin is filtered off and the filtrate is evaporated in vacuo at a temperature below 30° C. The crystalline residue is recrystallized from anhydrous methanol to yield 2.66 g of methyl di-N,N'-[N-(2-chloroethyl)-N-nitroso-carbamyl]-2,6-di-amino-2,6-di-deoxy-3-D-glucopyranoside. Yield: 57.7%. mp 151°∼153° C (decomp.). $[\alpha]_D^{25}$−5.5° (C=0.2, methanol). Analysis for $C_{13}H_{22}N_6O_8Cl_2$ (M.W. 461.26) (%) — C, 33.85; H, 4.81; N, 18.22; Cl, 15.37. Found: C, 33.91; H, 4.76; N, 18.18; Cl, 15.32.

The compound obtained in the above Example was pharmacologically recognized to be 5∼20% more active as an antitumor agent while it had reduced bone marrow toxicities in comparison with its a-anomer (i.e. the compound in example 3. This compound also possesses neither diabetogenic nor antibacterial activities.

EXAMPLE 8

1.93 g of methyl 2-amino-2-deoxy-3-D-glucopyranoside are dissolved in 20 ml of dimethylsulfoxide, and to this solution 1.2 g of 2-chloroethyl isocyanate are added dropwise at 25° C while stirring vigorously. Such stirring is continued for 30 minutes, while the completion of the reaction is checked by tlc. The reacted solution is evaporated in vacuo at a temperature below 40° C. The crystalline residue is recrystallized from isopropanol to yield 1.98 g of methyl N-carbamyl-N'-(2-chloroethyl)-2-amino 2-deoxy-3-D-glucopyranoside. Yield: 65%. mp 168°∼170° C. $[\alpha]_D^{25}$−28.4°(C=0.5, $H_2O$). Analysis for $C_{10}H_{19}N_2O_6Cl$ (M.W. 298.72) (%) — C, 40.21; H, 6.41; N, 9.38; Cl, 11.87. Found: C, 40.25; H, 6.45; N, 9.36; Cl, 11.93.

2.98 g of methyl N-carbamyl-N'-(2-chloroethyl)-2-amino-2-deoxy-3-D-glucopyranoside prepared in the same manner as described above in this Example are dissolved in 30 ml of a solution consisting of 50% acetic and 50% formic acids (1:1), and to this solution 0.8 g of sodium nitrite powder is slowly added at 0°∼5° C while stirring vigorously. The mixture is further stirred for 1 day. To this mixture 13 g of ion exchange resin are then added, followed by stirring for 30 minutes. The ion exchange resin is filtered off and the filtrate is evaporated in vacuo at a temperature below 30° C. The crystalline residue is recrystallized from isobutanol to yield 2.09 g of methyl N-carbamyl-N'-(2-chloroethyl)-N'-nitroso-2-amino-2 -deoxy-3-D-glucopyranoside. Yield: 63.8%. mp 152°∼154° C (decomp.). $[\alpha]_D^{25}$−4°(C=0.5, $H_2O$). Analysis for $C_{10}H_{18}N_3O_7Cl$ (M.W. 327.72) (%) — C, 36.65; H, 5.54; N, 12.82; Cl, 10.82. Found: C, 36.63; H, 5.49; N, 12.79; Cl, 10.90.

EXAMPLE 9

54.4 g of an anomeric mixture of n-butyl 2-amino-2-deoxy-D-glucopyranoside hydrochloride (1:1) are dissolved in 300 ml of water, and to this solution are added 100 ml of benzene, then 22 g of 2-chloroethyl isocyanate, 14.3 g of tripropylamine and 8 g of pyridine. The resulting mixture is heated under reflux, and the reaction solution is evaporated in vacuo. The crystalline residue is after washing with a little amount of ethanol, recrystallized from ethanol to yield 20.2 g of n-butyl N-carbamyl-N'-(2-chloroethyl)-2-amino-2-deoxy-3-D-glucopyranoside. Yield: 59.2%. mp 182°∼184° C. $[\alpha]_D^{25}$−43°(C=0.3, $H_2O$). Analysis for $C_{13}H_{25}N_2O_6Cl$ (M.W. 340.80) (%) — C, 45.82; H, 7.39; N, 8.22; Cl, 10.40. Found: C, 45.74; H, 7.34; N, 8.13; Cl, 10.44.

The washings and mother liquor both of which have been obtained in the above Example and which contain n-butyl N-carbamyl-N'-(2-chloroethyl)-2-amino-2-deoxy-α-D-glucopyranoside are combined and concentrated in vacuo. The concentrate is charged onto a silicagel column, and the adsorbed materials thereon are eluted with chloroform-ethanol (3:1), and this eluate is collected in 20 ml fractions. Tlc sampling [solvent: chloroform-ethanol (3:1)] of each fraction is analyzed to detect n-butyl N-carbamyl-N'-(2-chloroethyl)-2-amino-2-deoxy-α-D-glucopyranoside. The fractions containing the above mentioned compound are combined and evaporated in vacuo. The crystalline residue is washed with isopropanol to yield 15.5 g of n-butyl N-carbamyl-N'-(2-chloroethyl)-2-amino-2-deoxy-α-D-glucopyranoside. Yield: 45.5%. mp 135°∼137° C. $[\alpha]_D^{25}$+86° (C=0.3, $H_2O$). Analysis for $C_{13}H_{25}N_2O_6Cl$ (M.W. 340.80) (%) — C, 45.82; H, 7.39; N, 8.22; Cl, 10.40. Found: C, 45.89; H, 7.41; N, 8.15; Cl, 10.30.

3.41 g of n-butyl N-carbamyl-N'-(2-chloroethyl)-2-amino-2-deoxy-3-D-glucopyranoside obtained in the above Examples are dissolved in 40 ml of 20% acetic acid aqueous solution, and to this solution 0.95 g of sodium nitrite are added over 30 minutes, at 0°∼5° C, while stirring, and the reaction solution is allowed to stand at 0°∼5° C for 5 days. A further 0.15 g portion of sodium nitrite is added to the reaction solution, and again allowed to stand at 0°∼5° C for 2 days, while the completion of the reaction is checked by tlc. To the reacted solution are added 15 ml of ion exchange resin, followed by stirring for 1 hour while ice-cooling. The ion exchange resin is filtered and the filtrate is concentrated in vacuo at a temperature below 25° C to a syrup. The syrup is separated and purified with a silcagel column [the trade name "kieselgel-60"; developing solvent: chloroform-ethanol (9:1)]. The purified syrup thus obtained is crystallized using ether and petroleum ether. The resultant crystals are then dried in vacuo to give 2.17 g of n-butyl N-carbamyl-N'-(2-chloroethyl)-N'-nitroso-2-amino-2-deoxy-3-D-glucopyranoside. Yield: 58.7%. mp 110°∼112° C (decomp.). $[\alpha]_D^{25}$−30° (C=0.2, $H_2O$). Analysis for $C_{13}H_{24}N_3O_7Cl$ (M.W. 369.80) (%) — C, 42.22; H, 6,54; N, 11.36; Cl, 9.59. Found: C, 42.30; H, 6.51; N, 11.22; Cl, 9.74.

Likewise, employing 3.41 g of n-butyl N-carbamyl-N'-(2-chloroethyl)-2-amino 2-deoxy-α-D-glucopyranoside, 2.04 g of n-butyl N-carbamyl-N'-(2-chloroethyl)-N'-nitroso-2-amino-2-deoxy-α-D-glucopyranoside are obtained. Yield: 55.2%. mp 98°∼100° C (decomp.). $[\alpha]_D^{25}$+118° (C=1.0, $H_2O$). Analysis for $C_{13}H_{24}N_3O_7Cl$ (M.W. 369.80) (%) — C, 42.22; H, 6.54; N, 11.36; Cl, 9.59. Found: C, 42.14; H, 6.54; N, 11.42; Cl, 9.68.

The above mentioned α-and 3-anomers of this compound were pharmacologically recognized to have the same level of anitumor activity as the compounds mentioned in examples 1 and 4. Their bone marrow toxicities also showed the same low levels. These compounds also possess neither diabetogenic nor antibacterial activities.

EXAMPLE 10

2.57 g of dried n-propyl 6-amino-6-deoxy-α-D-glucopyranoside hydrochloride [mp 135° C (decomp.); $[\alpha]_D^{25}+60.7°$ (C=0.1, methanol); hygroscopic]are dissolved in 50 ml of absolute methanol. To this solution are then added 2.0 g of silver carbonate while icecooling with stirring. The mixture is stirred further for 1 hour, and after filtration, the reaction solution are cooled to −8° C. Into the solution is then added dropwise 1.26 g of 2-chloroethyl isocyanate while stirring, and such stirring is continued for 2 hours. The resultant solution is allowed to stand overnight at 5° C. The solution is, after decoloring with activated carbon, concentrated in vacuo. The concentrate is charged onto a silicagel column, and the absorped materials are eluted with chloroform-ethanol (5:1), and this eluate is collected in fractions. Tlc samplings of each fraction are analyzed to detect n-propyl N-carbamyl-N'-(2-chloroethyl)-6-amino-6-deoxy-α-D-glucopyranoside. The fractions containing the above-mentioned compound are combined and evaporated in vacuo to yield 1.80 g of a syrup. The syrup is crystallized using chloroform and petroleum ether. The crystals thus obtained are washed with chloroform-petroleum ether (1:1), and are dried in vaeuo, and thus 1.36 g of n-propyl N-carbamyl-N'-(2-chloroethyl)-6-amino-6-deoxy-α-D-glucopyranoside is obtained. Yield: 42.0%. mp 112°~113° C. $[\alpha]_D^{25}+26°$ (C=1.0, methanol). Rf 0.56 (tlc). IR (KBr): 1630 cm$^{-1}$ (C=0), 1580 cm$^{-1}$ (—NH), 848 cm$^{-1}$ (α-anomeric C$_1$-H). Analysis for C$_{12}$H$_{23}$N$_2$O$_6$Cl (M.W. 326.78) (%) — C, 44.11; H, 7.09; N, 8.57; Cl, 10.85. Found: C, 44.01; H, 7.15; N, 8.48; Cl, 10.62.

1.0 g of n-propyl N-carbamyl-N'-(2-chloroethyl)-6-amino-6-deoxy-α-D-glucopyranoside obtained in the above Example are dissolved in 30 ml of 20% acetic acid aqueous solution, to which 0.255 g of sodium nitrite are then added over 30 minutes, at 0°~5° C while stirring. The mixture is allowed to stand at 0°~5° C for 4 days and another 50 mg portion of sodium nitrite is added thereto, followed by a period in which it is allowed to stand again at 0°~5° C for 2 days. The completion of the reaction is checked by tlc. To the reaction solution are added 5 ml of ion exchange resin, and the mixture is stirred for 1 hr while ice-cooling. The ion exchange resin is filtered off and the filtrate is concentrated in vacuo at a temperature below 25° C to a syrup. The syrup is purified by a silicagel column [solvent: chloroform-ethanol (9:1)],and crystallized by using ether and petroleum ether. The crystals thus obtained are dried in vacuo and thereby 0.51 g of n-propyl N-carbamyl-N'-(2-chloroethyl)-N'-nitroso-6-amino-6-deoxy-α-D-glucopyranoside is obtained. Yield: 47%. mp 75° C (decomp.). Rf 0.63 (tlc). $[\alpha]_D^{25}+66°$ (C=0.1, methanol). Hygroscopic.

EXAMPLE 11

2.57 g of n-propyl 6-amino-6-deoxy-α-D-glucopyranoside hydrochloride are reacted with 1.26 g of 2-chloroethyl isocyanate in the same manner as described in example 10. The syrup thus obtained is dissolved in 40 ml of 20% acetic acid aqueous solution, to which 0.69 g of sodium nitrite are added over 30 minutes while stirring with ice-cooling. The stirring is continued for 1.5 hr, and the solution is allowed to stand at 0°~5° C for 2 days. To this solution are again added 0.27 g of sodium nitrite, and this solution is then allowed to stand at 0°~5° C for 2 days. Subsequently, the solution is worked up in the same manner as is described in example 10, and thereby 1.2 g of n-propyl N-carbamyl-N'-(2-chloroethyl)-N'-nitroso-6-amino-6-deoxy-α-D-glucopyranoside is obtained. Yield: 34.3%. mp 75° C (decomp.). $[\alpha]_D^{25}+66°$ (C = 0.1, methanol). Hygroscopic.

EXAMPLE 12

2.29 g of methyl 6-amino-6-deoxy-β-D-glucopyranoside hydrochloride are dissolved in 50 ml of methanol. To this 2.0 g of silver carbonate are added at 0°~5° C while stirring vigorously. Such stirring is continued for 1 hr, and the solution is filtered to remove the insoluble materials. The filtrate is cooled to − 5° C, and to this filtrate 1.26 g of 2-chloroethyl isocyanate are added dropwise while stirring. The mixture is further stirred for 2 hours and this is then allowed to stand at 0°~5° C overnight. The solution is, after decoloring with activated carbon, concentrated in vacuo to a syrup. Said syrup is charged onto a silicagel column, and the materials adsorbed thereon are eluted with chloroform-ethanol (4:1). The eluate is collected in fractions, and tlc samplings of each fraction are analyzed to detect methyl N-carbamyl-N'-(2-chloroethyl)-6-amino-6-deoxy-β-D-glucopyranoside. The fractions containing the above-mentioned compound are combined and concentrated in vacuo to a syrup, which is then crystallized using chloroform and petroleum ether. The crystals thus obtained are washed with chloroform-petroleum ether and dried in vacuo, thereby 1.66 g of methyl N-carbamyl-N'-(2-chloroethyl)-6-amino-6-deoxy-β-D-glucopyranoside is obtained. Yield: 55.5%. mp 169°~171° C. $[\alpha]_D^{25}-31°$ (C=0.5, H$_2$O). Analysis for C$_{10}$H$_{19}$N$_2$O$_6$Cl (M.W. 298.72) (%) — C,40.21; H, 6.41; N, 9.38; Cl, 11.87. Found: C, 40.15; H, 6.49; N, 9.44; Cl, 11.73.

2.99 g of methyl N-carbamyl-N'-(2-chloroethyl)-6-amino-6-deoxy-3-D-glucopyranoside prepared in the same manner is dissolved in 40 ml of 30% acetic acid aqueous solution, to which 0.9g of sodium nitrite is added over 30 minutes, at 0°~5° C while stirring. The mixture is allowed to stand at 0°~5° C overnight, while the completion of the reaction is checked by tlc. To the reacted solution is added 15 ml of ion exchange resin, and the mixture is stirred for 1 hour, while ice-cooling. The ion exchange resin is filtered off and the filtrate is concentrated in vacuo at a temperature below 25° C to a syrup. The syrup is purified by using a silicagel column [solvent: chloroform-ethanol (9:1)]. The syrup thus treated is crystallized by using ether and petroleum ether, and the resultant crystals are then dried in vacuo, and thereby 1.95 g of methyl N-carbamyl-N'-(2-chloroethyl)-N'-nitroso-6-amino-6-deoxy-β-D-glucopyranoside are obtained. Yield: 59.4% m.p. 109°–113° C. (decomp.). $[\alpha]_D^{25}-6°$ (C = 0.5, H$_2$O). Analysis for C$_{10}$H$_{18}$N$_3$O$_7$Cl (M.W. 327.72) (%)— C, 36.65, H, 5.54; N, 12.82; Cl, 10.82. Found: C, 36.73; H, 5.62; N, 12.74; Cl, 10.73.

The compound in the above Example was pharmacologically active and found to have higher antitumor activity and reduced bone marrow toxicity to the extent of 110~120% compared with its α-anomer (refer to Table II and III). The compound also possesses neither diabetogenic nor antibacterial activities.

What is claimed is:

1. An alkyl amino-glucopyranoside having the following formula:

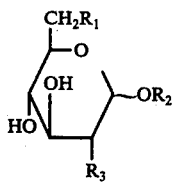 [I]

in which $R_1$ is an N-carbamyl-N'-(2-chloroethyl)-N'-nitroso-amino group, $R_2$ is an alkyl group having from 1 to 4 carbon atoms, and $R_3$ is an hydroxyl group or an N-carbamyl-N'-(2-chloro-ethyl)-N'-nitroso-amino group.

2. Compound, according to claim 1, wherein $R_3$ is an N-carbamyl-N'-(2-chloroethyl)-N'-nitroso-amino group.

3. An alkyl amino-gluocopyranoside having the following formula:

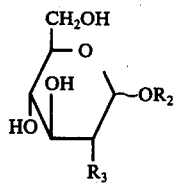 [II]

in which $R_3$ is an N-carbamyl-N'-(2-chloroethyl)-N'nitroso-amino group and $R_2$ is an alkyl group having from 1 to 4 carbon atoms.

4. Compound, according to claim 1, in which $R_2$ is methyl and said compound is α-anomer.

5. Compound, according to claim 1, in which $R_2$ is methyl and said compound is β-anomer.

6. Compound, according to claim 3, in which $R_2$ is methyl and said compound is α-anomer.

7. Compound, according to claim 3, in which $R_2$ is methyl and said compound is β-anomer.

8. Compound, according to claim 2, in which $R_2$ is methyl and said compound is α-anomer.

9. Compound, according to claim 2, in which $R_2$ is methyl and said compound is β-anomer.

10. Compound, according to claim 3, in which $R_2$ is n-butyl and said compound is α-anomer or β-anomer.

11. Compound, according to claim 1, in which $R_2$ is n-propyl and said compound is α-anomer.

* * * * *